(12) United States Patent
Marcu et al.

(10) Patent No.: US 11,350,907 B2
(45) Date of Patent: Jun. 7, 2022

(54) SINGLE CATHETER SYSTEM THAT PROVIDES BOTH INTRAVASCULAR ULTRASOUND AND FLUORESCENCE LIFETIME IMAGING

(71) Applicant: The Regents of the University of California, Oakland, CA (US)

(72) Inventors: Laura Marcu, Davis, CA (US); Julien Bec, Davis, CA (US); Diego R. Yankelevich, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 433 days.

(21) Appl. No.: 16/463,306

(22) PCT Filed: Nov. 30, 2017

(86) PCT No.: PCT/US2017/063880
§ 371 (c)(1),
(2) Date: May 22, 2019

(87) PCT Pub. No.: WO2018/102513
PCT Pub. Date: Jun. 7, 2018

(65) Prior Publication Data
US 2019/0374195 A1    Dec. 12, 2019

Related U.S. Application Data

(60) Provisional application No. 62/428,978, filed on Dec. 1, 2016.

(51) Int. Cl.
*A61B 8/12* (2006.01)
*A61B 5/00* (2006.01)
(Continued)

(52) U.S. Cl.
CPC ............ *A61B 8/12* (2013.01); *A61B 5/02007* (2013.01); *A61B 5/6852* (2013.01);
(Continued)

(58) Field of Classification Search
None
See application file for complete search history.

(56) References Cited

U.S. PATENT DOCUMENTS 5,039,193 A    8/1991 Snow et al.
6,272,376 B1   8/2001 Marcu et al.
(Continued)

OTHER PUBLICATIONS

International Search Report and Written Opinion from PCT Patent Application No. PCT/US2017/063880 dated Feb. 16, 2018 by the United States Patent Office.

*Primary Examiner* — Shahdeep Mohammed
(74) *Attorney, Agent, or Firm* — Park, Vaughan, Fleming & Dowler LLP (57) ABSTRACT

A multimodal intravascular catheter system includes a catheter with an optical channel and an electrical channel. A distal end of the catheter includes an optical element and an ultrasonic transducer, which are oriented orthogonally to a rotational axis of the catheter. A motor drive unit (MDU) is coupled to a proximal end of the catheter and includes a drive motor to rotate the catheter. The optical channel directs light from a pulsed UV laser source to the optical element, and returns an optical fluorescence signal from the optical element. A photodetector converts the returned optical fluorescence signal into an electrical fluorescence signal. An intravascular ultrasound (IVUS) processor is coupled to the ultrasonic transducer through the electrical channel, wherein the IVUS processor generates a drive signal for the ultrasound transducer, and processes echo information returned from the ultrasound transducer. Finally, a digitizer samples
(Continued)

the electrical fluorescence signal and associated echo information.

21 Claims, 6 Drawing Sheets (51) Int. Cl.
*A61B 8/08* (2006.01)
*A61B 8/00* (2006.01)
*G01N 21/63* (2006.01)
*A61B 5/02* (2006.01)

(52) U.S. Cl.
CPC .......... *A61B 8/0891* (2013.01); *A61B 5/0035* (2013.01); *A61B 5/0071* (2013.01); *A61B 5/6876* (2013.01); *A61B 8/4444* (2013.01); *A61B 8/5261* (2013.01); *G01N 21/63* (2013.01)

(56) References Cited

U.S. PATENT DOCUMENTS

| | | |
|---|---|---|
| 2009/0203991 A1 | 8/2009 | Papaioannou et al. |
| 2010/0249603 A1 | 9/2010 | Hastings et al. |
| 2014/0323860 A1 | 10/2014 | Courtney et al. |

SINGLE CATHETER SYSTEM THAT PROVIDES BOTH INTRAVASCULAR ULTRASOUND AND FLUORESCENCE LIFETIME IMAGING

RELATED APPLICATION

This application claims priority to U.S. Provisional Application No. 62/428,978, entitled "Apparatus and Methods for Intravascular Ultrasound Imaging and Fluorescence Lifetime Imaging," by inventors Laura Marcu, Julien Bec and Diego Yankelevich, the contents of which are incorporated by reference herein in their entirety.

GOVERNMENT LICENSE RIGHTS

This invention was made with Government support under Grant No. RO1 HL067377 awarded by the National Institutes of Health. The government has certain rights to the invention.

BACKGROUND

Field

The disclosed embodiments generally relate to catheter-based vascular-imaging techniques. More specifically, the disclosed embodiments relate to the design of a vascular-imaging system, which integrates both intravascular ultrasound (IVUS) imaging and fluorescence-lifetime imaging microscopy (FLIm) functionality into a single catheter.

Related Art

The majority of sudden acute cardiovascular events result from rupture or erosion of vulnerable plaques. The identification of these vulnerable plaques can facilitate interventional techniques and pharmacological therapies to reduce such events. Because angiography provides limited information about the nature of the plaque occluding a vessel, percutaneous coronary interventions (PCIs) assisted with imaging techniques have become an important tool for studying plaque progression and pathology. Optical coherence tomography (OCT) and intravascular ultrasound (IVUS) are the two most common intravascular imaging techniques used in catheterization laboratories with near-infrared spectroscopy (NIRS) recently introduced into clinical practice as well.

Unfortunately, the above-described intravascular imaging techniques have a number of shortcomings. IVUS is not able to detect rupture-prone thin-cap fibroatheromas (TCFAs) due to limited spatial resolution (>100 µm). Conversely, OCT has a spatial resolution of 10-20 µm and can detect thin caps and can also assess inflammation, but has limited imaging penetration depth and cannot reliably determine the size of deep plaque cores or outward remodeling, which are important indicators of plaque vulnerability. NIRS has the ability to detect lipid cores, but has limited sensitivity for other proteins of interest, such as collagen and elastin.

Because each of the above-listed intravascular imaging modalities by itself is limited in one way or another, multimodal imaging wherein two or more modalities complement one another to allow simultaneous assessment of plaque structure and composition would be extremely beneficial. For example, researchers have demonstrated that fluorescence-lifetime imaging microscopy (FLIm) techniques based on UV-light induced tissue autofluorescence can be used with IVUS to better identify distinct coronary plaque pathologies. (See H. Fatakdawala, D. Gorpas, J. W. Bishop, J. Bec, D. Ma, J. A. Southard, K. Margulies, and L. Marcu, "Fluorescence lifetime imaging combined with conventional intravascular ultrasound for enhanced assessment of atherosclerotic plaques: An ex vivo study in human coronary arteries," J. of Cardiovasc. Trans. Res. 1-11 (2015).)

However, the only previously existing intravascular catheter is a research tool, which is only able to gather FLIm and IVUS images sequentially. This makes it hard to co-register the FLIm and IVUS images because during heartbeats, the catheter translates longitudinally within the blood vessel. These registrations issues can limit the effectiveness of combining FLIm and IVUS images to identify vulnerable plaques within a blood vessel.

Hence, what is needed is a multimodal vascular-imaging technique, which does not suffer from the above-described shortcomings of existing multimodal imaging techniques.

SUMMARY

The disclosed embodiments relate to the design of a multimodal intravascular catheter system. This system includes a catheter with an optical channel and an electrical channel, wherein a distal end of the catheter includes an optical element and an ultrasonic transducer, which are oriented orthogonally to a rotational axis of the catheter. A motor drive unit (MDU) is coupled to a proximal end of the catheter, wherein the MDU includes a rotary optical coupling for the optical channel, a rotary electrical coupling for the electrical channel, and a drive motor to rotate the catheter. An ultraviolet (UV) pulsed laser source is coupled to the optical element through the optical channel so that the optical channel directs light from the UV laser source to the optical element, and returns an optical fluorescence signal from the optical element. A photodetector converts the returned optical fluorescence signal into an electrical fluorescence signal. An IVUS processor is coupled to the ultrasonic transducer through the electrical channel, wherein the IVUS processor generates a drive signal for the ultrasound transducer and processes associated echo information returned from the ultrasound transducer. Finally, a digitizer (oscilloscope or specialized/customized board/electronics) samples the electrical fluorescence signal and associated echo information.

In some embodiments, the system also includes: a wavelength-selection module, which splits the optical fluorescence signal returned from the optical element into multiple spectral bands. It also includes a set of optical delay lines that insert different delays into each of the multiple bands before the multiple bands feed into the photodetector, thereby enabling the digitizer to time-resolve fluorescence decay from multiple spectral bands simultaneously.

In some embodiments, the system additionally includes an image-processing mechanism that processes the sampled electrical fluorescence signal and associated echo information, wherein the image-processing mechanism co-registers structural images of blood vessels obtained from IVUS echo information with multispectral FLIm images of the same blood vessels obtained from the electrical fluorescence signal.

In some embodiments, the optical element comprises a curved mirror that reflects and focuses light from the UV laser source in a direction orthogonal to the rotational axis of the catheter.

In some embodiments, the optical channel in the catheter comprises a single multi-mode optical fiber that carries light from the UV laser source to the optical element, and returns the optical fluorescence signal from the optical element.

In some embodiments, the rotary optical coupling comprises a stationary optical fiber and a rotating optical fiber, which are butt-coupled and enclosed in a ferrule.

In some embodiments, the ultrasonic transducer comprises a piezoelectric ultrasonic transducer that both generates an ultrasonic acoustic signal and receives returned echo information.

In some embodiments, the rotary electrical coupling comprises an inductive coupling.

In some embodiments, the photodetector comprises a photomultiplier tube (PMT).

DETAILED DESCRIPTION

The following description is presented to enable any person skilled in the art to make and use the present embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present embodiments. Thus, the present embodiments are not limited to the embodiments shown, but are to be accorded the widest scope consistent with the principles and features disclosed herein.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium. Furthermore, the methods and processes described below can be included in hardware modules. For example, the hardware modules can include, but are not limited to, application-specific integrated circuit (ASIC) chips, field-programmable gate arrays (FPGAs), and other programmable-logic devices now known or later developed. When the hardware modules are activated, the hardware modules perform the methods and processes included within the hardware modules.

Overview

The disclosed embodiments combine catheter-based intravascular ultrasound (IVUS) with fiber-based fluorescence-lifetime imaging microscopy (FLIm) in a single-catheter system that detects and characterizes morphology and biochemical composition of atherosclerotic vessels in vivo. This multimodal catheter system is composed of a catheter, a motor drive unit (MDU) and acquisition electronics for FLIm and IVUS data. The catheter integrates both IVUS and FLIm components into a single imaging core. The ultrasound components of the catheter are composed of one or more single-element ultrasonic transducers, which are oriented orthogonally to a rotation axis of the catheter, and are connected to a hub through a transmission line (coaxial cable or twisted pair). The hub provides electrical connections to the MDU to transfer IVUS signals to and from the catheter. The FLIm elements of the catheter are comprised of: an optical connector providing high-efficiency optical coupling with the MDU; a fiber optic transmitting the optical signal to and from the imaging core's distal end; and an optical element that deflects the beam orthogonally to the rotation axis of the catheter. Note that this optical element can be composed of a reflective prism, an angled polished surface, a reflective lens or gradient index lenses. Moreover, the optical element and ultrasonic transducers are mounted in a rigid distal probe housing that enables precise colocation of Ultrasound and optical beams.

The MDU enables rotation of the imaging core as well as rotary coupling of both electrical (for ultrasound) and optical (for FLIm) channels. Rotary electrical coupling can be achieved by inductive coupling or electrical slip rings, whereas optical coupling can be achieved with face-to-face coupling or can include collimating optics.

The data acquisition electronics of the ultrasound channel comprise a pulser and a receiver connected to a signal-sampling element, which is itself connected to a processing unit capable of displaying ultrasound images. In an exemplary embodiment, the FLIm system is composed of a short (<1 ns) pulsed ultraviolet (UV) (355 nm) laser, a dichroic element configured to direct the light from a UV laser to a sample path composed of multi-mode fiber optics, which are coupled to the FLIm path of the catheter through the MDU. Note that other excitation wavelengths can be used instead of 355 nm—provided that a tunable laser is available. This will allow us to sample the arteries at distinct depths and excite different fluorophores.

A fluorescence signal generated at the vessel wall is collected by the same fiber and crosses the first dichroic. It is then spectrally separated into different channels by a series of dichroic mirrors and bandpass filters. The contributions from each of the channels are delayed by optical delay lines of different lengths, and are connected to a fast photodetector (e.g., a microchannel plate photomultiplier tube, MCP-PMT). The electrical signal generated by the photodetector is then sampled by a high-speed digitizer and the corresponding samples are sent to a processing unit to extract multispectral fluorescence intensity and decay parameters. Separate IVUS and FLIm processing units can communicate with each other so as to generate co-registered and IVUS images. Alternatively, the IVUS and FLIm signals can be processed for display by a shared processing unit.

Figure 1:
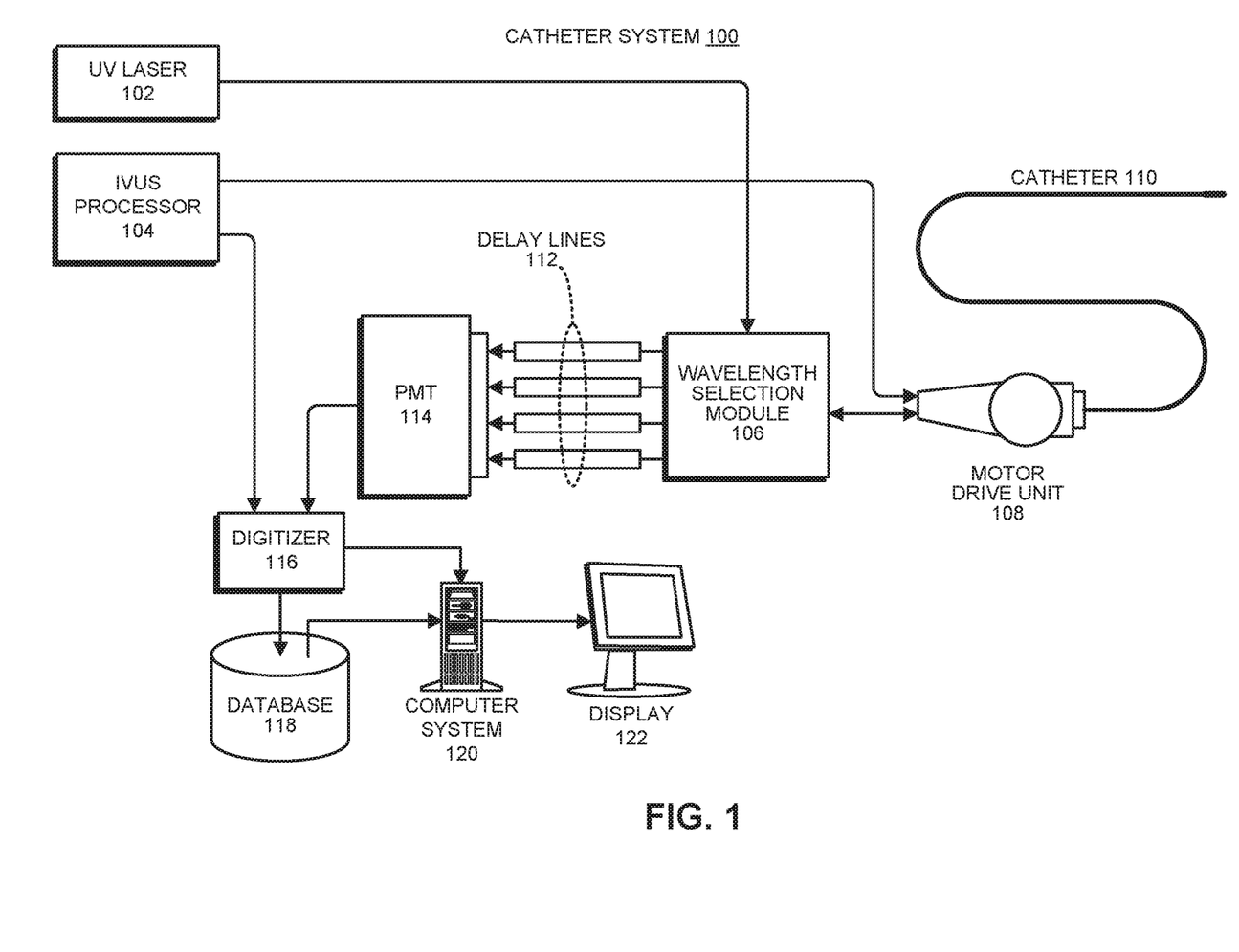
FIG. 1 illustrates a catheter system that facilitates multimodal vascular imaging in accordance with the disclosed embodiments.

As illustrated in FIG. 1, an exemplary embodiment of this bi-modal catheter system 100 was developed by modifying a Boston Scientific iLab™ IVUS system and is composed of: a custom IVUS/FLIm rotational catheter 110; a modified Boston Scientific motor drive unit (MDU) 108; and data acquisition and display units for both the IVUS and FLIm sub-systems. This imaging system is able to display IVUS images in real-time using a clinical interface, and includes a 3.7 Fr IVUS/FLIm catheter. The Boston Scientific IVUS MDU 108 is modified to accommodate an optical channel, which is connected to a wavelength selection module (WSM) 106. WSM 106 facilitates both coupling of the pulsed excitation light from UV laser 102 into the optical channel of catheter 110, and spectral decomposition of the returned fluorescence signal from the optical channel using four spectral bands. As illustrated in FIG. 1, a signal from each of four spectral bands is sent to a photomultiplier tube (PMT) 114 using different lengths of optical delay lines 112, which facilitates measurements over four wavebands using a single PMT 114. When acquiring bi-modal data, co-registration is ensured by sampling both FLIm and IVUS signals using a single digitizer 116. These digitized signals are processed for display using a computer system 120 to generate images, which are presented to a user through a display 122.

In an exemplary embodiment, the size (3.7 Fr) of the FLIm/IVUS catheter 110 is compatible with coronary imaging. Moreover, the IVUS performance (central frequency and bandwidth) is similar to a standard 40 MHz OptiCross™ catheter. Also, the modified MDU 108 provides a robust interface with the catheter, with optical coupling losses of less than 1 dB through MDU 108.

The system illustrated in FIG. 1 facilitates scans of a 20 mm section of a blood vessel in five seconds with a rotation speed of 1800 rpm. This provides 25,000 independent multispectral fluorescence lifetime point measurements of the blood vessel surface (20 kHz laser repetition rate, 4 time average per point), which are co-registered with IVUS data.

Data analysis software executing on computer system 120 generates intensity en face images derived from FLIm within seconds following the scan. Moreover, fast data processing based on the Laguerre technique enables the computation and display of lifetime maps from all four spectral channels to be generated in less than two minutes following the end of the scan.

Connections within the MDU

Figure 2:
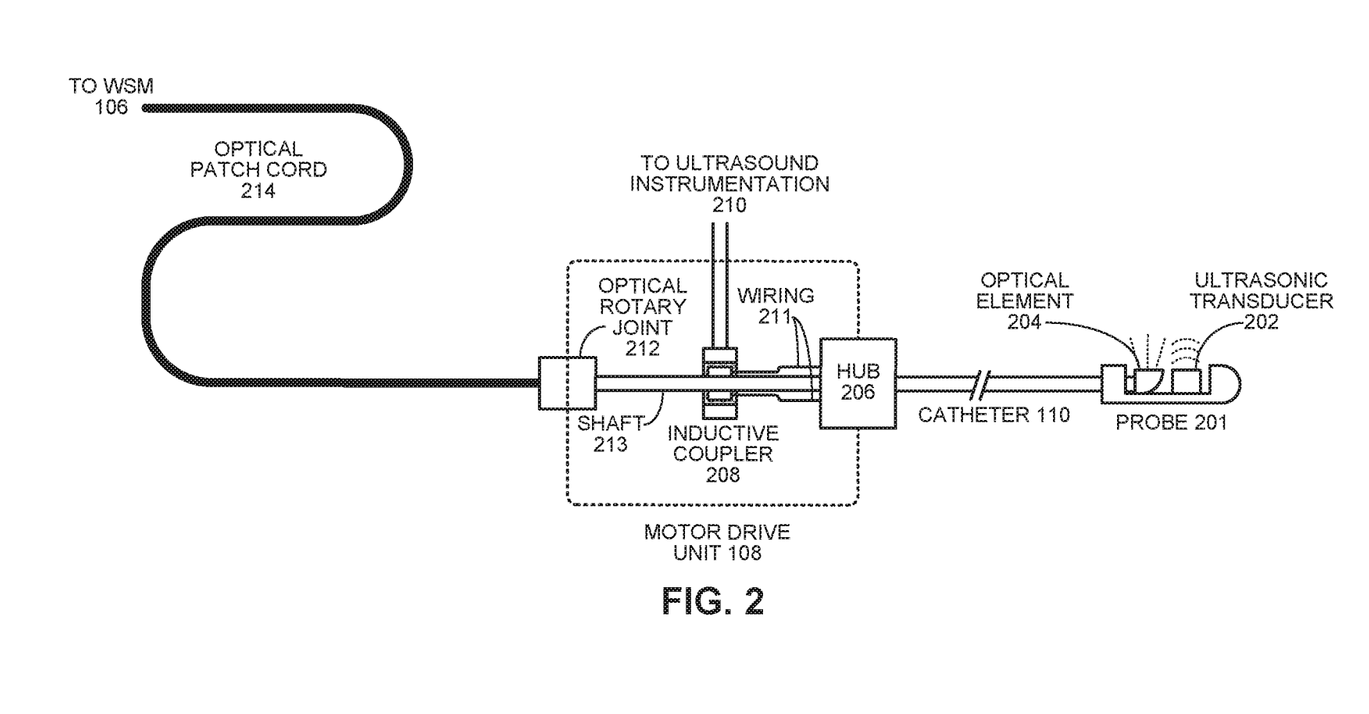
FIG. 2 illustrates optical and electrical connections within a motor drive unit (MDU) in accordance with the disclosed embodiments.

FIG. 2 illustrates various optical and electrical connections within motor drive unit (MDU) 108 in accordance with the disclosed embodiments. As illustrated in FIG. 2, the distal end of catheter 110 includes a probe 201, which includes an ultrasonic transducer 202, such as a piezoelectric ultrasonic transducer that both generates an ultrasonic acoustic signal and receives returned echo information. Probe 201 also includes an optical element 204 comprising a lens or prism. Note that ultrasonic transducer 202 and optical element 204 are configured in a fixed orientation to generate substantially overlapping ultrasonic and UV beams. The distal end of catheter 110 feeds into a hub 206, which is part of MDU 108. Hub 206 includes an optical coupler (not shown) between an optical fiber catheter 110 and a section of optical fiber located in a rotating shaft 213, which is mounted on bearings within MDU 108. Hub 206 also connects to wiring 211 that provides connections from an electrical channel carrying ultrasonic signals in catheter 110 (not shown) to a rotary port of inductive coupler 208. A corresponding stationary port of inductive coupler 208 communicates electrical signals with ultrasound instrumentation 210 located in IVUS processor 104. Finally, a proximal end of rotating shaft 213 feeds into an optical rotary joint 212, which couples optical signals from catheter 110 with an optical patch cord 214 that feeds into WSM 106.

Optical Coupling in the MDU

Figure 3A:
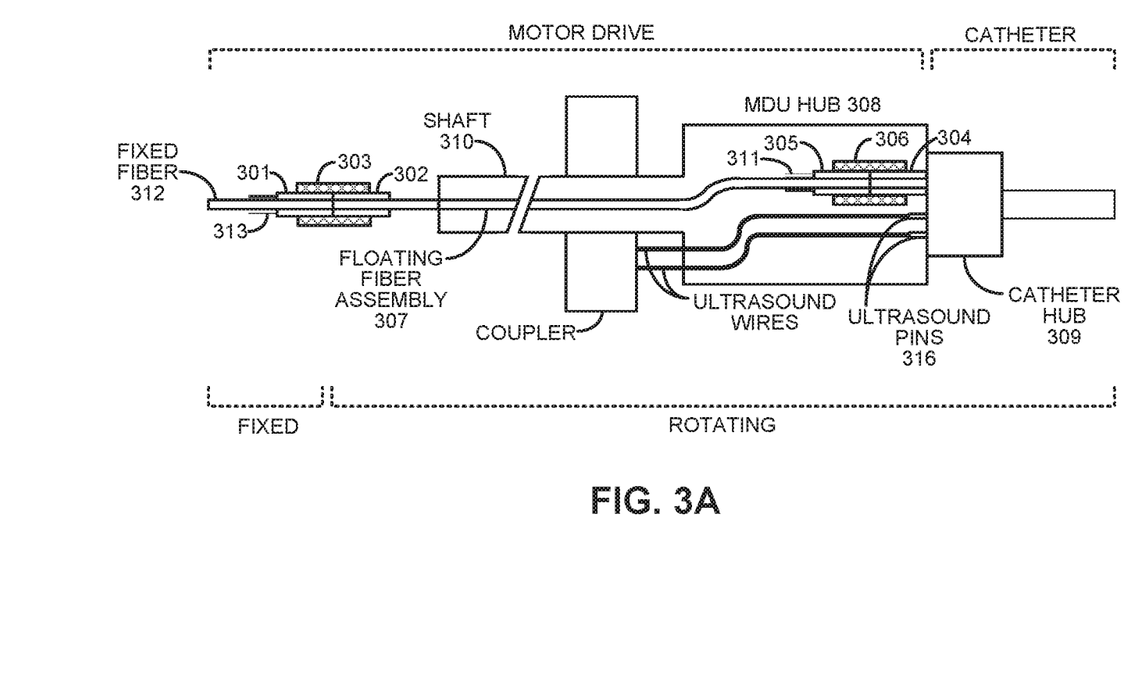
FIG. 3A illustrates the structure of an optical rotary joint in accordance with the disclosed embodiments.

FIG. 3A illustrates additional details about the structure of catheter hub interface 206, shaft 213 and optical rotary joint 212 in accordance with the disclosed embodiments. Note that two optical interfaces are implemented in MDU 108: (1) a coupling between the MDU 108 and catheter 110; and (2) a rotary coupling within MDU 108 between a floating fiber assembly 307, which rotates with the catheter 110, and fixed fiber optic patch cord 114, which is connected to the rest of the system. For that purpose, a floating fiber assembly 307 is located inside of a shaft 310 and provides an optical interface between a fixed fiber 312 and a catheter hub 309.

During operation, catheter hub 309 is mated with an MDU hub 308, which is located at the end of shaft 310. Two or more ultrasound pins (with associated sockets) 316, which are part of the MDU hub 308 and catheter hub 309, provide electrical connections between MDU 108 and catheter hub 309 for ultrasound signals. Optical coupling between catheter hub 309 and MDU hub 308 is provided by the insertion of a catheter hub ferrule 306, which surrounds the fiber optic, into an alignment sleeve 304 until it contacts a ferrule 305, which is located at the distal end of floating fiber assembly 307. To provide good coupling and to accommodate for geometrical tolerances, floating fiber assembly 307 is pushed against catheter hub ferrule 306 by a preload spring 311. The optical transmission of the coupling between floating fiber assembly and catheter hub is improved by optical gel.

Optical coupling between the floating fiber assembly 307 and the fixed fiber 312 is performed by enclosing a fixed ferrule 301, which terminates the fixed fiber, and a rotating ferrule 302, which terminates the floating fiber assembly 307, into an alignment sleeve 303. Note that fixed ferrule 301 and rotating ferrule 302 are "butt-coupled" within sleeve 304, and a gel is provided to facilitate optical coupling and reduce frictional forces associated with the coupling. Moreover, fixed ferrule 301 is pushed by a preloaded spring 313 against rotating ferrule 302 to provide a light mating force, such that ferrules 301 and 302 are kept in contact in response to movements of floating fiber assembly 307.

Optical Element

Figure 3B:
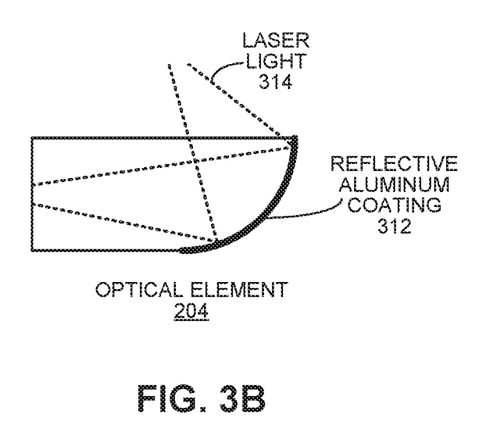
FIG. 3B illustrates the structure of an optical element, which is located at the distal end of the catheter in accordance with the disclosed embodiments.

FIG. 3B illustrates the structure of an optical element 204, which is located at the distal end of the catheter in accordance with the disclosed embodiments. As illustrated in FIG. 3B, optical element 204 comprises a curved mirror that implements an optical lens with a reflective aluminum coating 312, which reflects and focuses laser light 314 from the UV laser 102 in a direction orthogonal to the rotational axis of catheter 110. By using a focusing lens instead of a prism, the system concentrates the excitation light pulse and improves collection efficiency. This makes it possible to perform imaging operations using a thinner optical fiber, which is more flexible and can more easily navigate through small blood vessels. Moreover, because the optical lens is implemented using a curved mirror, the lens can be easily made broadband by using an appropriate reflective material, which facilitates imaging across multiple spectral bands.

The focusing lens illustrated in FIG. 3B can be fabricated in a micro-array of lenses at the wafer level through laser machining. This micro-array of lenses can then be coated with a reflective material, such as aluminum or dielectric reflective coating. Finally, the micro-array can be cut using a saw into rows of lenses and then into individual lenses.

Process of Operating the Multimodal Catheter System

Figure 4:
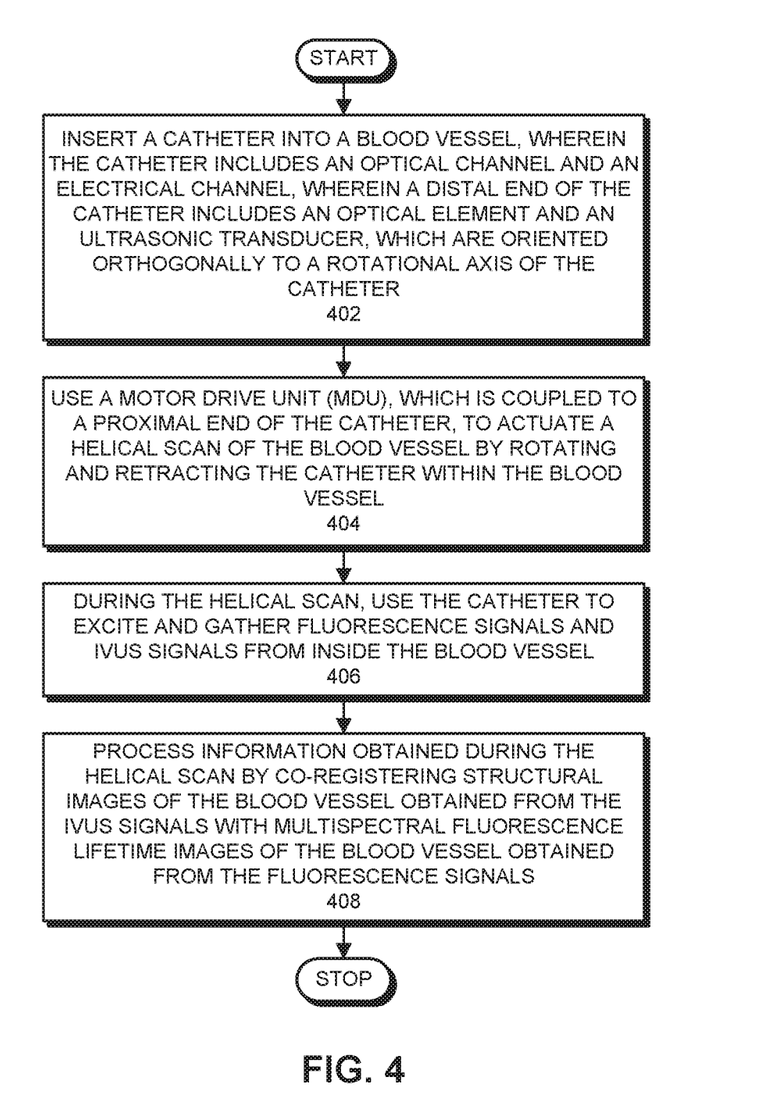
FIG. 4 presents a flow chart illustrating operations involved in operating a multimodal catheter system in accordance with the disclosed embodiments.

FIG. 4 presents a flow chart illustrating operations involved in operating a multimodal catheter system in accordance with the disclosed embodiments. First, a catheter is inserted into a blood vessel, wherein the catheter includes an optical channel and an electrical channel, and wherein a distal end of the catheter includes an optical element and an ultrasonic transducer, which are oriented orthogonally to a rotational axis of the catheter (step 402). Next, an MDU, which is coupled to a proximal end of the catheter, is used to actuate a helical scan of the blood vessel by rotating and retracting the catheter within the blood vessel (step 404). During the helical scan, the catheter is used to excite and gather fluorescence signals and IVUS signals from inside the blood vessel (step 406). Finally, information obtained during the helical scan is processed by co-registering structural images of the blood vessel obtained from the IVUS signals with multispectral fluorescence lifetime images of the blood vessel obtained from the fluorescence signals (step 408).

Figure 5:
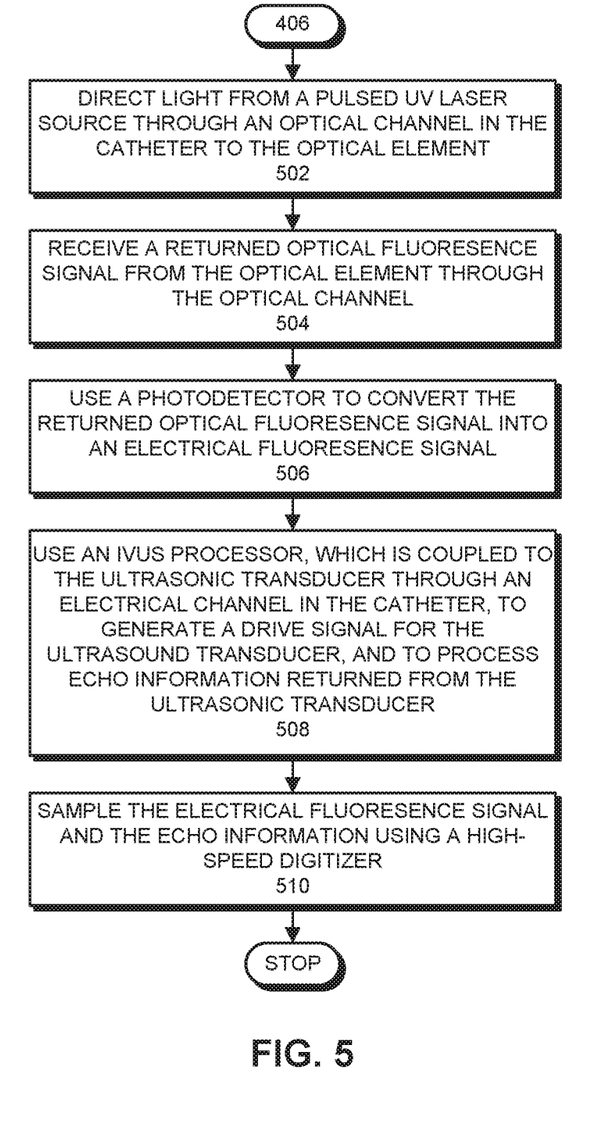
FIG. 5 presents a flow chart illustrating operations performed during a helical scanning process in accordance with the disclosed embodiments.

FIG. 5 presents a flow chart illustrating operations performed during the helical scanning process in accordance with the disclosed embodiments. First, the system directs light from a pulsed UV laser source through an optical channel in the catheter to the optical element (step 502). Next, the system receives a returned optical fluorescence signal from the optical element through the optical channel (step 504). The system then uses a photodetector to convert the returned optical fluorescence signal into an electrical fluorescence signal (step 506). While the optical signals are being generated and processed, the system uses an IVUS processor, which is coupled to the ultrasonic transducer through an electrical channel in the catheter, to generate a drive signal for the ultrasound transducer, and to process echo information returned from the ultrasonic transducer (step 508). Finally, the system samples the electrical fluorescence signal and echo information using a high-speed digitizer (step 506).

CONCLUSION

The disclosed embodiments integrate IVUS and FLIm imaging techniques into a single catheter to acquire co-registered structural and biochemical information in vivo in blood vessels, without the need for exogenous contrast agents. Integration of both imaging modalities is achieved in a manner that ensures that the performance of the IVUS component is not adversely impacted by the addition of FLIm capability. This type of bi-modal catheter system can be used to access coronary arteries using standard percutaneous coronary intervention techniques in common clinical settings.

The combination of FLIm with a morphological imaging modality such as IVUS is important, because FLIm alone cannot provide morphometric information about lumen size, geometry or direct measurement of lesion size. When projected onto a vessel lumen boundary identified by IVUS, the dimensions of FLIm features can be precisely assessed.

Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

The foregoing descriptions of embodiments have been presented for purposes of illustration and description only. They are not intended to be exhaustive or to limit the present description to the forms disclosed. Accordingly, many modifications and variations will be apparent to practitioners skilled in the art. Additionally, the above disclosure is not intended to limit the present description. The scope of the present description is defined by the appended claims.

What is claimed is:

1. A multimodal intravascular catheter system, comprising:
    a catheter including an optical channel and an electrical channel, wherein a distal end of the catheter includes an optical element and an ultrasonic transducer, which are oriented orthogonally to a rotational axis of the catheter;
    a motor drive unit (MDU) coupled to a proximal end of the catheter, wherein the MDU includes a rotary optical coupling for the optical channel, a rotary electrical coupling for the electrical channel, and a drive motor to rotate the catheter;
    an ultraviolet (UV) pulsed laser source, which is coupled to the optical element through optical channel so that the optical channel directs light from the UV laser source to the optical element, and returns an optical fluorescence signal from the optical element;
    a wavelength-selection module (WSM) configured to receive the optical fluorescence signal returned from the optical element and split the optical fluorescence signal into multiple spectral bands;
    a set of optical delay lines of different lengths configured to insert different delays into each of the multiple spectral bands;
    a photodetector, which converts the multiple spectral bands of the returned optical fluorescence signal into an electrical fluorescence signal;
    an intravascular ultrasound (IVUS) processor, which is coupled to the ultrasonic transducer through the electrical channel, wherein the IVUS processor generates a drive signal for the ultrasound transducer, and processes echo information returned from the ultrasound transducer; and
    at least one high-speed digitizer that samples the electrical fluorescence signal and the echo information, wherein having the WSM and the set of optical delay lines of different lengths before the photodetector enables using single photodetector to measure the multiple spectral bands, and enables the high-speed digitizer to time-resolve fluorescence decay from multiple spectral bands simultaneously.

2. The multimodal intravascular catheter system of claim 1, further comprising an image-processing mechanism that processes the sampled electrical fluorescence signal and echo information, wherein the image-processing mechanism co-registers structural images of blood vessels obtained from intravascular ultrasound (IVUS) echo information with multispectral fluorescence-lifetime imaging microscopy (FLIm) images of the same blood vessels obtained from the electrical fluorescence signal.

3. The multimodal intravascular catheter system of claim 1, wherein the optical element comprises a curved mirror that reflects and focuses light from the UV laser source in a direction orthogonal to the rotational axis of the catheter.

4. The multimodal intravascular catheter system of claim 1, wherein the optical channel in the catheter comprises a single multi-mode optical fiber that carries light from the UV laser source to the optical element, and returns the optical fluorescence signal from the optical element.

5. The multimodal intravascular catheter system of claim 1, wherein the rotary optical coupling comprises a stationary optical fiber and a rotating optical fiber, which are butt-coupled and enclosed in a ferrule.

6. The multimodal intravascular catheter system of claim 1, wherein the ultrasonic transducer comprises a piezoelectric ultrasonic transducer that both generates an ultrasonic acoustic signal and receives returned echo information.

7. The multimodal intravascular catheter system of claim 1, wherein during operation, the system performs a helical scan of a blood vessel by simultaneously rotating and retracting the catheter within the blood vessel while sampling multispectral fluorescence information and ultrasonic echo information.

8. The multimodal intravascular catheter system of claim 1, wherein the rotary electrical coupling comprises an inductive coupling.

9. The multimodal intravascular catheter system of claim 1, wherein the photodetector comprises a photomultiplier tube (PMT).

10. A method for operating a multimodal intravascular catheter system, comprising:
  operating a catheter, which is configured to be inserted into a blood vessel, wherein the catheter includes an optical channel and an electrical channel, and wherein a distal end of the catheter includes an optical element and an ultrasonic transducer, which are oriented orthogonally to a rotational axis of the catheter;
  wherein operating the catheter comprises using a motor drive unit (MDU), which is coupled to a proximal end of the catheter, to actuate a helical scan of the blood vessel by rotating and retracting the catheter within the blood vessel, wherein the MDU includes a rotary optical coupling for the optical channel, a rotary electrical coupling for the electrical channel, and a drive motor to rotate the catheter; and
  during the helical scan of the blood vessel,
    directing light from a pulsed ultraviolet (UV) laser source through the optical channel to the optical element;
    receiving a returned optical fluorescence signal from the optical element through the optical channel;
    splitting the returned optical fluorescence signal into multiple spectral bands;
    using a set of optical delay lines of different lengths to insert different delays into each of the multiple spectral bands;
    using a photodetector to convert the multiple spectral bands of the returned optical fluorescence signal into an electrical fluorescence signal; and
    using an intravascular ultrasound (IVUS) processor, which is coupled to the ultrasonic transducer through the electrical channel, to generate a drive signal for the ultrasound transducer, and to process echo information returned from the ultrasonic transducer; and
  using at least one high-speed digitizer to sample the electrical fluorescence signal and the echo information, wherein splitting the returned optical fluorescence signal into multiple spectral bands and inserting different delays into each of the multiple spectral bands before using the photodetector enables using a single photodetector to measure the multiple spectral bands, and enables the high-speed digitizer to time-resolve fluorescence decay from multiple spectral bands simultaneously.

11. The method of claim 10, further comprising using an image-processing mechanism to process the sampled electrical fluorescence signal and echo information, wherein during the processing, the image-processing mechanism co-registers structural images of blood vessels obtained from intravascular ultrasound (IVUS) echo information with multispectral fluorescence-lifetime imaging microscopy (FLIm) images of the same blood vessels obtained from the electrical fluorescence signal.

12. The method of claim 10, wherein the optical element comprises a curved mirror that reflects and focuses light from the UV laser source in a direction orthogonal to the rotational axis of the catheter.

13. The method of claim 10, wherein the optical channel in the catheter comprises a single multi-mode optical fiber that carries light from the UV laser source to the optical element, and returns the optical fluorescence signal from the optical element.

14. The method of claim 10, wherein the rotary optical coupling comprises a stationary optical fiber and a rotating optical fiber, which are butt-coupled and enclosed in a ferrule.

15. The method of claim 10, wherein the ultrasonic transducer comprises a piezoelectric ultrasonic transducer that both generates an ultrasonic acoustic signal and receives returned echo information.

16. The method of claim 10, wherein during the helical scan of the blood vessel, the method simultaneously rotates and retracts the catheter within the blood vessel while sampling multispectral fluorescence information and ultrasonic echo information.

17. The method of claim 10, wherein the rotary electrical coupling comprises an inductive coupling.

18. The method of claim 10, wherein the photodetector comprises a photomultiplier tube (PMT).

19. A multimodal intravascular catheter system, comprising:
  a catheter including an optical channel and an electrical channel, wherein a distal end of the catheter includes an optical element and an ultrasonic transducer, which are oriented orthogonally to a rotational axis of the catheter;
  a motor drive unit (MDU) coupled to a proximal end of the catheter, wherein the MDU includes a rotary optical coupling for the optical channel, a rotary electrical coupling for the electrical channel, and a drive motor to rotate the catheter;
  a laser source, which is coupled to the optical element through optical channel so that the optical channel directs light from the laser source to the optical element, and returns an optical fluorescence signal from the optical element;
  a wavelength-selection module (WSM) configured to receive the optical fluorescence signal returned from the optical element and split the optical fluorescence signal into multiple spectral bands;
  a module (WSM) configured to receive the optical fluorescence signal returned from the optical element and split the optical fluorescence signal into multiple spectral bands;

a set of optical delay lines of different lengths configured to insert different delays into each of the multiple spectral bands;

a photodetector, which converts the multiple spectral bands of the returned optical fluorescence signal into an electrical fluorescence signal;

an intravascular ultrasound (IVUS) processor, which is coupled to the ultrasonic transducer through the electrical channel, wherein the IVUS processor generates a drive signal for the ultrasound transducer, and processes echo information returned from the ultrasound transducer; and at least one high-speed digitizer that samples the electrical fluorescence signal and the echo information, wherein having the WSM and the set of optical delay lines of different lengths before the photodetector enables using a single photodetector to measure the multiple spectral bands, and enables the high-speed digitizer to time-resolve fluorescence decay from multiple spectral bands simultaneously.

20. The multimodal intravascular catheter system of claim 19, wherein the laser source emits a visible wavelength.

21. The multimodal intravascular catheter system of claim 19, wherein the laser source emits more than one excitation wavelength.

* * * * *

UNITED STATES PATENT AND TRADEMARK OFFICE
CERTIFICATE OF CORRECTION

PATENT NO. : 11,350,907 B2
APPLICATION NO. : 16/463306
DATED : June 7, 2022
INVENTOR(S) : Laura Marcu et al.

It is certified that error appears in the above-identified patent and that said Letters Patent is hereby corrected as shown below:

In the Claims

In Claim 19 (at Column 10, Line 64) please delete "a module (WSM) configured to receive the optical fluorescence signal returned from the optical element and split the optical fluorescence signal into multiple spectral bands;"

Signed and Sealed this
Sixteenth Day of August, 2022

Katherine Kelly Vidal
*Director of the United States Patent and Trademark Office*